United States Patent
Kuth et al.

(10) Patent No.: US 8,447,380 B2
(45) Date of Patent: May 21, 2013

(54) METHOD FOR DIAGNOSIS OF FUNCTIONAL LUNG ILLNESSES

(75) Inventors: Rainer Kuth, Höchstadt (DE); Sabine Rupprecht, Uttenreuth (DE); Thomas Rupprecht, Uttenreuth (DE); Maren Zapke, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1257 days.

(21) Appl. No.: 11/597,078

(22) PCT Filed: May 17, 2004

(86) PCT No.: PCT/EP2004/005300
§ 371 (c)(1),
(2), (4) Date: Jul. 16, 2008

(87) PCT Pub. No.: WO2005/112757
PCT Pub. Date: Dec. 1, 2005

(65) Prior Publication Data
US 2008/0269592 A1  Oct. 30, 2008

(51) Int. Cl.
*A61B 5/08* (2006.01)
(52) U.S. Cl.
USPC .......... 600/413; 600/410; 600/415; 600/532; 600/533

(58) Field of Classification Search
USPC ............... 600/410, 413, 415, 532; 324/318
See application file for complete search history.

(56) References Cited

U.S. PATENT DOCUMENTS

| | | | |
|---|---|---|---|
| 6,338,836 B1 | 1/2002 | Kuth et al. | |
| 6,370,415 B1 * | 4/2002 | Weiler et al. | 600/410 |
| 6,650,924 B2 | 11/2003 | Kuth et al. | |
| 6,790,183 B2 * | 9/2004 | Murphy | 600/532 |
| 7,539,539 B1 * | 5/2009 | Bharmi | 607/20 |
| 2002/0180439 A1 * | 12/2002 | Lee | 324/318 |
| 2003/0055331 A1 | 3/2003 | Kotmel et al. | |
| 2006/0264736 A1 * | 11/2006 | Ehman et al. | 600/410 |

OTHER PUBLICATIONS

"Measuring Quantitative Regional Lung Ventilation by Alveolar Ventilation Imaging (AVI)—Phantom Data and Results of a Feasibility Study in 50 Patients," Topf et al., ISMRM 2004, May 2004.

* cited by examiner

Primary Examiner — Tse Chin
Assistant Examiner — Vani Gupta
(74) Attorney, Agent, or Firm — Schiff Hardin LLP

(57) ABSTRACT

In a method for diagnosing functional lung illnesses, image exposures of the lungs are obtained at various phase points in time of the respiration of a subject, such as at maximum inhalation and maximum expiration, and the image exposures are segmented and at least two of the image exposures are compared on a segment-by-segment basis to identify a change in tissue density between the compared segments, as an indicator of lung functioning.

17 Claims, 3 Drawing Sheets

METHOD FOR DIAGNOSIS OF FUNCTIONAL LUNG ILLNESSES

BACKGROUND OF THE INVENTION

1. Field of the Invention

The present invention relate to methods for diagnosing functional long illnesses, particularly with the use of images of the lungs of a subject obtained with a medical imaging modality.

2. Description of the Prior Art

For the diagnosis and therapy of lung illnesses it is necessary to record spatially resolved and time-resolved functional parameters of the lungs using measurement technology. In healthy people the lung is nearly homogeneous, meaning that macroscopically the lung is uniformly filled with fresh air upon inhalation and uniformly emptied upon exhalation. The very thin lung tissue is permeated by a few large and many small blood vessels and bronchi. In a series of different illnesses of the lung, specific areas do not participate in the exchange with fresh air. Such areas can, for example, be filled with mucus, for example in the case pneumonia lung inflammation. Such areas can already be detected in part with conventional x-ray and MR methods.

In the case of certain other illnesses, however, parts of the lung are filled with air without an exchange with the fresh inhaled air ensuing, or the exchange is at least hindered. With asthma, a narrowing of the air passages leads to an at least delayed, but mostly insufficient exhalation of the air. This leads not only to a correspondingly reduced capacity of the lung but also over longer periods of time to a permanent damage of the lung tissue (emphysema). The most frequent causes for this in young patients are asthmatic illnesses or allergies and metabolic illnesses (cystic fibrosis) and others which lead to a local restriction or even collapse of the air passages and, over the long term, to a deterioration of the lung.

In order to be able to detect such functional lung illnesses, among other things it is known to introduce hyper-polarized gases into the lung as a contrast agent. These gases exhibit a nuclear spin and are polarized in a static magnetic field with irradiation of the patient during inhalation. The concentration of the hyper-polarized atoms can then be detected in the MR scanner. Unfortunately, the suitable isotopes are very rare or extremely difficult to provide (for example $He_3$ forms only 0.01% of naturally-occurring helium and, due to its low density, escapes forever after the release into the atmosphere). Alternative isotopes provide only a relatively low contrast due to the low resonance frequency and the poor degree of hyper-polarization. This is the case, for example, for $Xe_{129}$ with a frequency of approximately ¼ the proton frequency and a hyper-polarization degree of only maximally 10%, compared to approximately 60% for $He_3$. Moreover, the apparatus expenditure in the MR scanner given the use of hyper-polarized gases is not in consequential. Due to the low resonance frequency relative to protons, a dedicated RF system is required, which incurs additional costs. Moreover, an HPG MR measurement can be repeated only in a limited manner since these gases supply no contribution to the oxygen saturation and therefore can be tolerated to a limited degree in patients, in particular those with limited lung function. Alternatively, an examination with radioactive gases (lung scintigraphy) is possible.

SUMMARY OF THE INVENTION

An object of the present invention is to provide a method that allows a fast, inexpensive, radiation-free and better spatially-resolved detection of functional defects of the lung as well as a precise acquisition of the effect of therapies.

This object is achieved in accordance with the invention by a method wherein image data of the lung are acquired at various phase points of the respiration (in particular at maximum inhalation and maximum exhalation), at which the change of the tissue density is determined by a section-by-section comparison. While an increase of the tissue density occurs upon exhalation form normally functioning lung tissue, this is not the case in regions in which no exchange with the fresh inhalation air ensues and which consequently do not change their volume upon inhalation and exhalation.

In the case of asthmatic or otherwise diseased lung tissue, the density decreases only in a delayed manner and/or to a small degree upon exhalation.

According to a first exemplary embodiment of the present invention, the tissue density change can be determined by determining the proton density as a measure of the tissue density, by means of an imaging system, for example a spiral CT apparatus, or with an MR apparatus.

The determinability of the alveolar ventilation by the determination of the proton density is based on the fact that the measurement signal in practice arises exclusively from the walls of the alveoli and the remaining lung tissue while the air contained in them supplies nearly no contribution to the measurement signal. If one assumes that the entire MR signal is $$S_1 = \sum_{i=1}^{n_1} S_{ni},$$

wherein $S_{ni}$ is the measurement signal that is generated by one of the $n_1$ alveoli and the tissue surrounding it, this signal changes upon inhalation because the entire measurement volume under consideration is filled by $n_2$ alveoli, with $n_2$ being smaller than $n_1$. As stated the signal of a single alveole remains the same due to the unchanged tissue proportion, so the entire MR signal $S_2$ is $$S_2 = \sum_{i=1}^{n_2} S_{ni}.$$

Since $S_{ni}$ is constant, $S_2$ deviates from $S_1$ and enables the calculation of the alveolar ventilation.

The alveolar ventilation (V) is provided by:

$$V = (S_1 - S_2)/(S_1 - S_R).$$

wherein $S_R$ is the signal of the background noise (the inhaled air).

Further function data such as the ventilation speed, the tidal volume, the residual volume or the reserve capacity, which can then likewise be graphically presented as well in a corresponding manner, can be calculated from the temporal change of the ventilation.

In a further embodiment of the invention, 2D images or 3D images of the lung can be segmented into macroscopic areas, with the difference with regard to the air being determined as a measurement signal for each area and being compared with the measurement signal of the same area at another phase point of the respiration.

In order to be able to compare the same areas with one another, which areas can shift very significantly upon inhalation and exhalation, in an embodiment of the invention anatomical features (such as, for example, the blood vessels, the diaphragm or the bronchi) in the lung are segmented and the areas are associated with the features, and for localization of the measurement volumes to be compared with one another the shifts of the areas are determined using the shift of the anatomical features. This detection of the respective identical areas using the position between specific blood vessels can also be utilized in the same manner as that the expansion or compression is calculated from the shift of the areas between the images acquired at different phase points of the respiration.

In a further embodiment, a color-coded map of the areas is superimposed on the anatomical image of the thorax, with each area colored corresponding to the proton density change and/or the speed of the change.

Moreover, the present invention also enables an improved quantitative evaluation of the effectiveness of an asthma therapy with the aid of functional magnetic resonance of the lung (fMRL). Asthma therapies are very expensive and do not have a good success rate.

A quantitative evaluation of the effectiveness of an asthma therapy is described, for example, in U.S. Pat. No. 6,338,836 B1, in which hyper-polarized gases as well as asthma provokers with and without therapeutics are administered to the asthma patients, and the respectively generated MR images are compared with one another. However, this known evaluation method is subject to the limitation that it can only be applied a few times since a hyper-polarized gas supplies no contribution to the oxygen saturation and therefore has the aforementioned low tolerability.

According to the invention the examination for evaluation of the effectiveness of aromatherapeutics is implemented with the aid of a functional magnetic resonance examination of the lung, whereby after an fMRL without additives to the inhalation gas, a substance for inhalation that includes an asthma provoker and/or a therapeutic is administered to the patient. Preferably that has an a dose is used effect that is not measurable over the entirety of the lungs with a lung function measuring modality because the change lies below the biologically produced margin of deviation.

A measurement without administration of additional inhalation substances is subsequently implemented in order to determine changes relative to the first measurement, for example by difference formation over the entire lung. A new map of the lung is thereby displayed that indicates where deviations have occurred.

In a fourth step it is subsequently decided whether the second step should be repeated with an increased dose or whether the examination can be ended. If necessary further examination steps with increased (with regard to the dose) inhalation substances, and subsequent control measurements, can be added.

DESCRIPTION OF THE PREFERRED EMBODIMENTS

Figure 1:
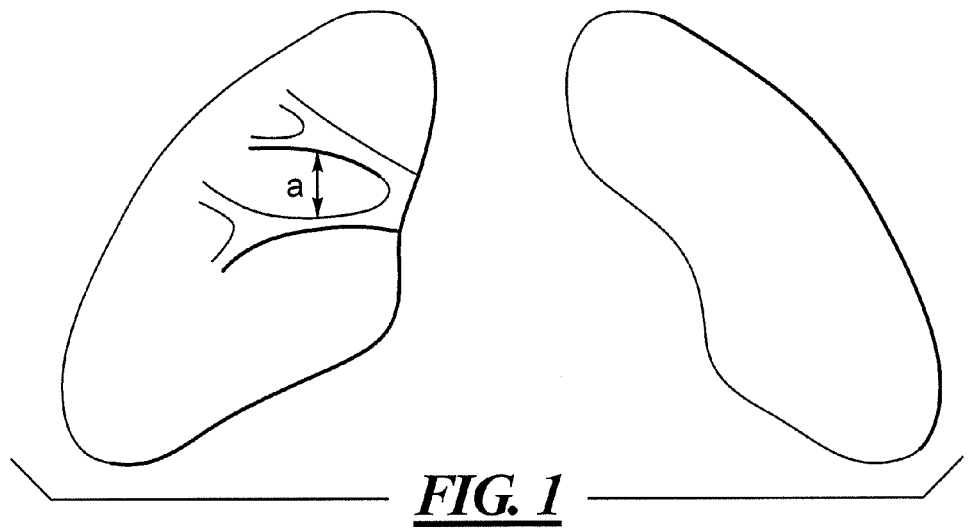
FIG. 1 is a schematic representation of a lung in the exhaled state.
Figure 2:
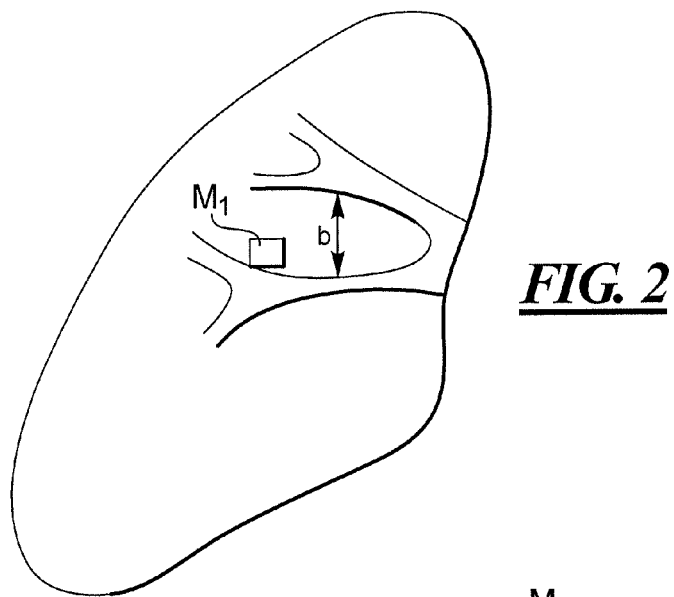
FIG. 2 is a schematic representation of a lung in the inhaled state.

The lung is shown at maximum exhalation in FIG. 1 and at maximum inhalation in FIG. 2. To produce these images the patient is positioned in an MR scanner such that the lung lies in the FOV. An MR exposure is generated at each of various phase points of the respiration, in the shown exemplary embodiment at maximum inhalation and maximum exhalation. The change of the proton density dependent on the phase point of the respiration (or the time) provides a measure for the homogeneity and thus also for possible functional lung illnesses.

For this purpose the 2D image of the lung can be subdivided in a computer into macroscopic areas, for example 100 squares. For each square the computer then determines the signal difference in comparison to the air at inhalation and exhalation. The computer also segments the blood vessels of the lung and associates the segments with these vessels.

In order to compare the same lung region in each of the inhaled state and exhaled state, thus for example in order to compare the measurement volume M1 in FIG. 1 in an appropriate manner with the same measurement volume M1 in FIG. 2 in spite of the displacement that occurs upon inhalation (in which measurement volume M1 in FIG. 2 the schematically indicated blood vessels 1 and 2 as well as the remaining tissue have significantly altered their separation (b>a)), the segmentation described above is effected with regard to the vessels or other features such as, for example, the bronchi or the diaphragm. The computer then determines the displacement of each segment between inhalation and exhalation and the density change.

Figure 3:
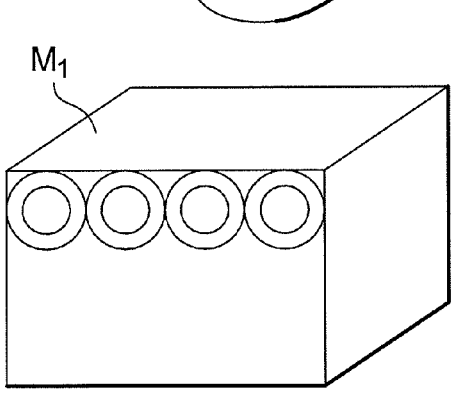
FIG. 3 illustrates a cubic measurement volume in the exhaled state that is filled by n1 alveoli.
Figure 4:
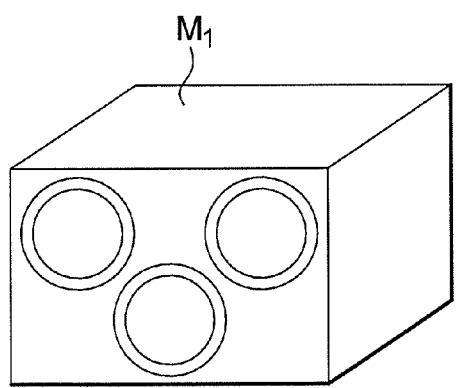
FIG. 4 is a schematic representation of the same cubic measurement volume in the inhaled state, in which this measurement volume is filled by n2 alveoli.

FIGS. 3 and 4 respectively show a measurement volume, for example the measurement volume M1 in FIGS. 1 and 2 in the inhaled state and in the exhaled state. This cubic measurement volume M1 is filled by $n_1$ alveoli in the exhaled state according to FIG. 1. The total MR signal $S_2$ is $$S_1 = \sum_{i=1}^{n_1} S_{ni}.$$

Assuming that it is healthy lung tissue, the cubic measurement volume is filled by fewer (namely $n_2$) alveoli in the inhaled state. The signal of a single alveole remains the same since an unchanged tissue proportion is present. The entire MR signal is $$S_2 = \sum_{i=1}^{n_2} S_{ni}.$$

It is important that $S_{ni}$ is thereby constant.
The alveolar ventilation (V) is provided by $$V=(S_1-S_2)/(S_1-S_R).$$

wherein $S_R$ is the signal of the background noise (the inhaled air).

Figure 5:
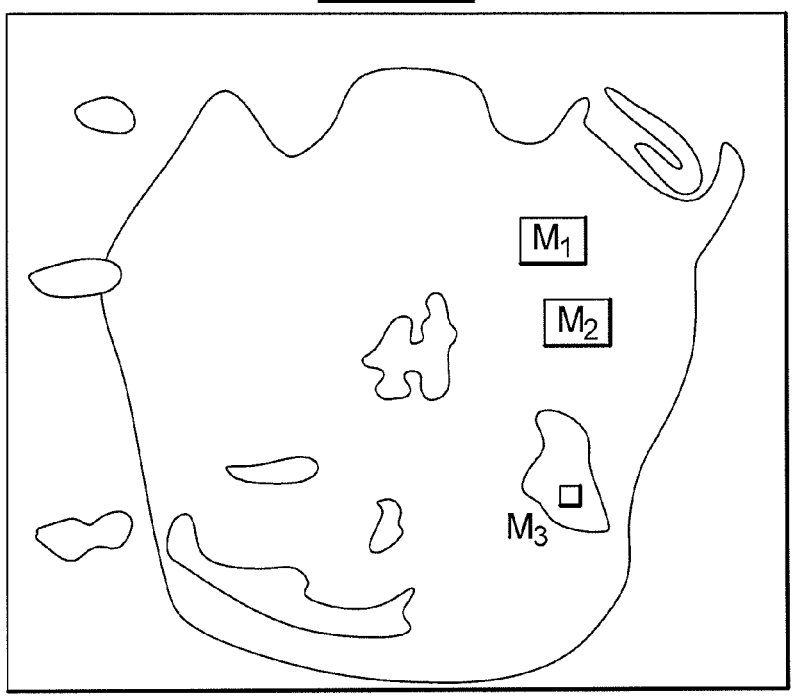
FIG. 5 is an MR image of a lung, in which various regions 1, 2 and 3 in a lobe of the lung are marked that should be considered separately.

FIG. 5 shows an MR image, whereby three measurement regions M1, M2 and M3 in which different lung functions are present are marked in the right drawn lobe of the lung.

Figure 6:
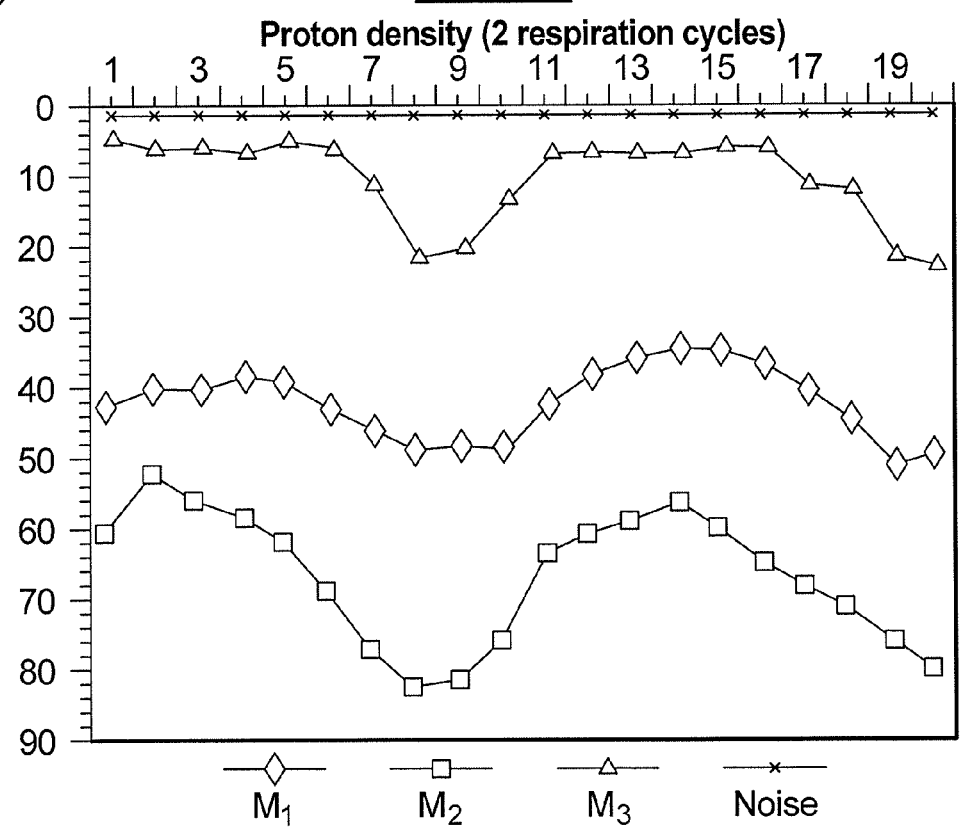
FIG. 6 shows the proton density over two respiration cycles in the regions 1, 2 and 3 from FIG. 5.

FIG. 6 shows the proton density over two respiration cycles, respectively in the region of the areas M1, M2 and M3, whereby the noise signal (which is negligible in practice) is additionally also plotted.

Figure 7:
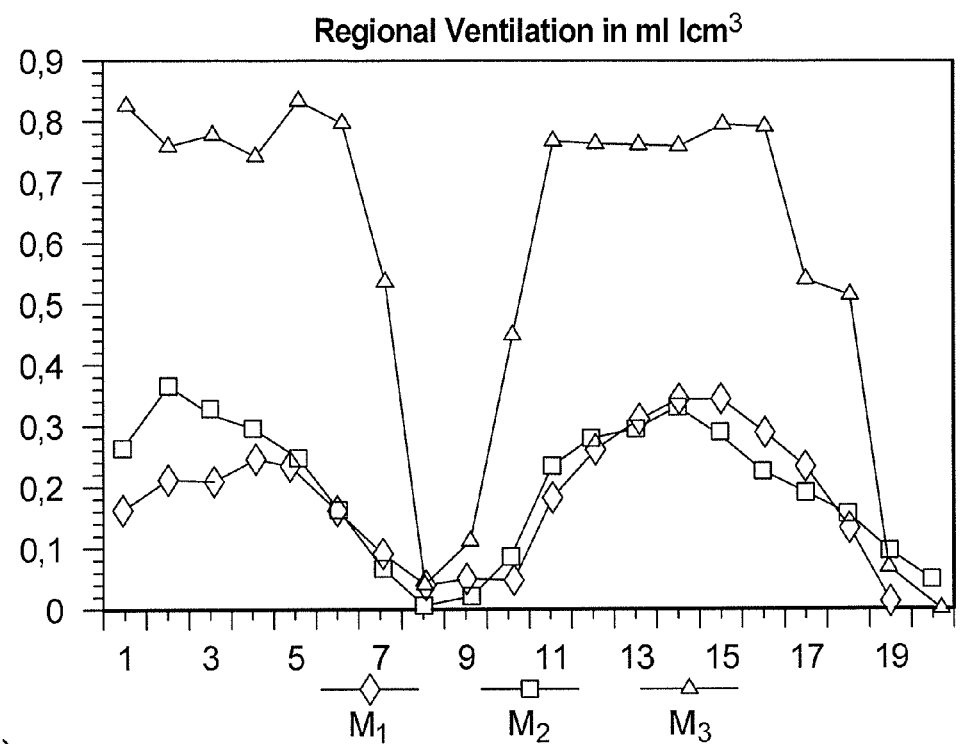
FIG. 7 shows the calculated results of the regional ventilation in ml/cm³, determined from the measurements.

FIG. 7 shows the regional ventilation (which can be calculated from the measurement data) in ml/cm$^3$, which indicates significant differences for the three lung regions represented by the measurement volumes M1, M2 and M3.

The determined data can be shown in the manner by the computer superimposing a color-coded map of the segments on the anatomical image of the thorax, wherein each color segment is inked corresponding to the proton density change and/or the speed of the change.

In place of the determination of the proton density change and the tissue density change with the method described in the preceding, the computer can also directly determine the expansion of the lung segments from the displacement of the blood vessels and then combine these measurement values with the previously specified measurement. If one assumes that emphysema is present at a specific point, this means that both adjacent blood vessels do not change their separation, in contrast to a convergence in the remaining lung region. This enables a determination of the expansion of the corresponding lung segments.

The computer takes into account not only the maximum inhalation and exhalation but also phase points in-between. The local inhalation speed and exhalation speed can be determined from this and be shown alternatively or additionally, for example color-coded.

The invention represents a new paradigm for the diagnosis of functional lung illnesses. Due to the short measurement time and the absent radiation exposure for the patient, it can be used cheaply and also in the framework of screenings. Over the long term juvenile ventilation defects lead to types of emphysemas, meaning a rapid degradation of the lung vitality. These patients then already require an overnight oxygen feed as of 50 or 60 years of age and, due to the high susceptibility to, for example, different pneumonias (lung inflammations), have a low life expectancy.

Figure 8:
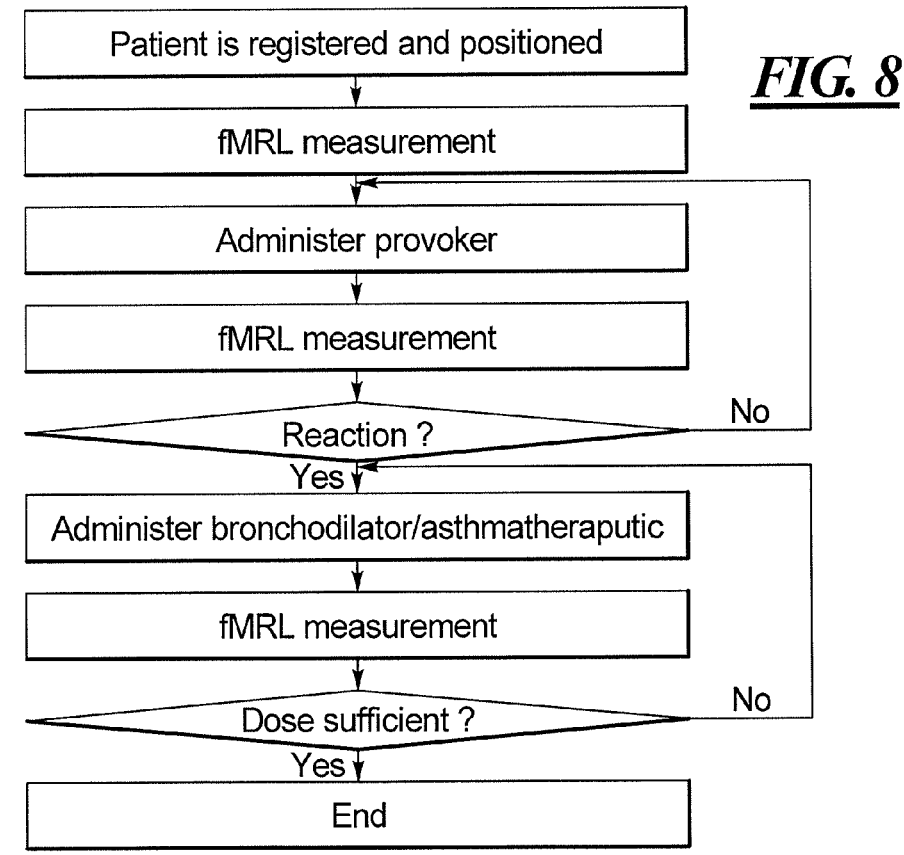
FIG. 8 is a flowchart for an evaluation of an asthma therapy in accordance with the aid of the inventive method using functional magnetic resonance of the lung (fMRL).

FIG. 8 shows a flowchart of a method for quantitative evaluation of the effectiveness of an asthma therapy in accordance with the invention.

The patient is initially registered and positioned in an MR scanner. A functional MR measurement of the lung (fMRL) subsequently ensues for determination of the initial position. A substance for inhalation that comprises an asthma provoker is subsequently administered to the patient, and preferably with a dose having an effect that is not measurable over the entire lung with a lung function measuring modality because the change lies below the biologically-provided margin of deviation. An fMRL measurement subsequently ensues in turn. If no reaction occurs due to the asthma provoker, the stage of the provoker administration is repeated with a higher dose and the preceding measurement cycle is implemented again. If a reaction due to the asthma provoker occurs, a bronchodilator/asthma therapeutic is administered and subsequently measured in turn in order to establish whether the asthma therapeutic has responded. If the dose was not sufficient or the agent was not effective, an administration of the asthma therapeutic at a higher dose or with a different substance can ensue again. If the dose was sufficient such that a satisfactory improvement has occurred, the evaluation method is ended.

Although modifications and changes may be suggested by those skilled in the art, it is the invention of the inventors to embody within the patent warranted heron all changes and modifications as reasonably and properly come within the scope of their contribution to the art.

We claim as our invention:

1. A method for diagnosing functional lung illnesses comprising the steps of:
   operating a medical imaging apparatus to acquire, at each of a plurality of different respiration phase points in time in a succession during respiration of a subject, an image exposure of the lungs of the subject; and
   in a processor supplied with the image exposures, automatically electronically dividing each of said image exposures into a plurality of segments and automatically electronically comparing corresponding segments in at least two of said image exposures to automatically identify a change in tissue density of tissue in the lungs between the compared segments, and making an indication of said change available in electronic form at an output of said processor.

2. A method as claimed in claim 1 comprising generating said image exposures of the lungs of the subject at respective respiration phase points in time representing maximum inhalation and maximum expiration.

3. A method as claimed in claim 1 comprising acquiring said image exposures with a magnetic resonance apparatus as said medical imaging apparatus, and automatically determining a change in proton density between the compared segments as said change of said tissue density.

4. A method as claimed in claim 1 comprising, from said change in tissue density, automatically electronically calculating lung function data selected from the group consisting of ventilation, tidal volume, residual volume, and reserve capacity.

5. A method as claimed in claim 1 wherein the step of automatically electronically segmenting each of said image exposures comprises dividing each of said image exposures into a plurality of macroscopic areas, and wherein the step of comparing corresponding segments comprises comparing corresponding macroscopic areas in at least two of said image exposures by determining a signal representing air in the tissue contained in the compared macroscopic areas.

6. A method as claimed in claim 5 comprising determining corresponding macroscopic areas to be compared in said at least two of said image exposures by segmenting anatomical features in said at least two of said image exposures, associating at least one macroscopic area in each of said at least two image exposures with the segmented anatomical features therein, and localizing respective macroscopic areas in said at least two of said image exposures by determining displacement of said anatomical features in said at least two of said image exposures.

7. A method as claimed in claim 5 comprising identifying displacement of adjacent anatomical features in said at least two of said image exposures, and determining at least one of expansion or compression of said macroscopic area from displacement of said adjacent anatomical features.

8. A method as claimed in claim 5 comprising automatically electronically generating a color-coded image of the tissue density in the respective macroscopic areas, and superimposing said color-coded image on an anatomical image of the thorax of the subject.

9. A method as claimed in claim 5 comprising, for each macroscopic area, automatically electronically calculating a rate of change of the tissue density and generating a color-coded image of the rate of change of the respective macroscopic area and superimposing said color-coded image on an anatomical image of the thorax of the subject.

10. A method as claimed in claim 1 comprising displaying at least one of said image exposures at an electronic display and placing an electronic cursor at a selected point of a lung in the displayed image exposure, and, from said change in tissue density, representing a respiration function at said point.

11. A method as claimed in claim 1 comprising generating said image exposures with near-field magnetic resonance system.

12. A method as claimed in claim 1 comprising calculating a ventilation value from said change in said tissue density, and automatically electronically calculating an overall function of the lungs as a sum of all ventilation values.

13. A method as claimed in claim 1 comprising additionally conducting a perfusion measurement of the subject and calculating a ventilation coefficient V from said change in said tissue density and calculating a perfusion coefficient Q from said perfusion measurement, and calculating V/Q.

14. A method as claimed in claim 13 comprising conducting said perfusion measurement as a measurement selected from the group consisting of spin labeling perfusion measurements and contrast agent perfusion measurements.

15. A method as claimed in claim 1 comprising generating a video real-time representation of the respiration of the subject from the changes of said tissue density.

16. A method as claimed in claim 1 comprising generating said image exposures as fMRL exposures and alternatingly administering an asthma provoker and a therapeutic agent to the subject for obtaining respective ones of said image exposures, and wherein the step of comparing at least two of said image exposures comprises comparing an image exposure obtained with said asthma provoker and an image exposure obtained with said therapeutic agent to quantitatively evaluate effectiveness of an asthma therapy involving said therapeutic agent.

17. A method as claimed in claim 16 comprising administering said asthma provoker and said therapeutic agent at a dose having an effect that is not measurable over an entire lung with a lung function measuring modality.

\* \* \* \* \*